US011938174B2

(12) United States Patent
Broom et al.

(10) Patent No.: US 11,938,174 B2
(45) Date of Patent: *Mar. 26, 2024

(54) COMPOSITIONS AND METHODS USEFUL FOR THE TREATMENT OF NEUROMYELITIS OPTICA SPECTRUM DISORDERS

(71) Applicant: Takeda Pharmaceutical Company Limited, Osaka (JP)

(72) Inventors: Colin Broom, Devon, PA (US); Jeffrey Dayno, Maple Glen, PA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 303 days.

This patent is subject to a terminal disclaimer.

(21) Appl. No.: 17/018,954

(22) Filed: Sep. 11, 2020

(65) Prior Publication Data

US 2021/0236607 A1  Aug. 5, 2021

Related U.S. Application Data

(63) Continuation of application No. 16/293,134, filed on Mar. 5, 2019, now Pat. No. 10,786,557, which is a continuation of application No. 14/539,405, filed on Nov. 12, 2014, now Pat. No. 10,272,142.

(60) Provisional application No. 61/903,643, filed on Nov. 13, 2013.

(51) Int. Cl.
| | | |
|---|---|---|
| *A61K 38/55* | (2006.01) | |
| *A61K 35/16* | (2015.01) | |
| *A61K 38/57* | (2006.01) | |
| *A61K 45/06* | (2006.01) | |
| A61K 39/395 | (2006.01) | |
| C07K 16/18 | (2006.01) | |
| C07K 16/28 | (2006.01) | |

(52) U.S. Cl.
CPC .............. *A61K 38/57* (2013.01); *A61K 35/16* (2013.01); *A61K 38/55* (2013.01); *A61K 45/06* (2013.01); *A61K 39/3955* (2013.01); *C07K 16/18* (2013.01); *C07K 16/28* (2013.01)

(58) Field of Classification Search
CPC ........ A61K 38/57; A61K 35/16; A61K 38/55; A61K 45/06; A61K 39/3955; C07K 16/18; C07K 16/28; A61P 25/00; A61P 25/28; A61P 37/02; A61P 37/06; A61P 43/00

See application file for complete search history.

(56) References Cited

U.S. PATENT DOCUMENTS

| | | |
|---|---|---|
| 10,272,142 B2 | 4/2019 | Broom et al. |
| 2002/0160491 A1 | 10/2002 | Jian et al. |
| 2014/0378653 A1 | 12/2014 | Meuth et al. |
| 2016/0166660 A1 | 6/2016 | Nolte et al. |

FOREIGN PATENT DOCUMENTS

| | | |
|---|---|---|
| EP | 263110 A1 | 4/1988 |
| WO | WO 2013/137912 A2 | 9/2013 |

OTHER PUBLICATIONS

Cocchio et al., "Cinryze, a Human Plasma-Derived C1 Esterase Inhibitor for Prophylaxis of Hereditary Angioedema", P&T: A Peer-Reviewed Journal for Formulary Management, 34(6): 293-328 (2009).
Collongues, et al., "Current and future treatment approaches for neuromyelitis optica", Ther. Adv. Neurol. Disorders, 4(2): 111-121 (2011).
Cheng et al., "Acute and subacute inflammation of the optic nerve and its sheath: clinical features in Chinese patients", Hong Kong Med J, 18(2) :115-122, (Apr. 2012).
European Medicines Agency publication No. 602545, "Cinryze: CHMP assessment report for pediatric use studies submitted according to Article 46 of the Regulation (EC) No. 1901/2006" published Jul. 25, 2013.
International Search Report/Written Opinion, issued by the European Patent Office dated Feb. 6, 2015, in corresponding PCT/US2014/065180, filed Nov. 12, 2014.
Jarius et al., "Contrasting disease patterns in seropositive and seronegative neuromyelitis optica: A multicenter study of 175 patients," J. Neuroinflammation, 9:14, 1-17, (2012).
Kim, et al., "Clinical Efficacy of Plasmapheresis in patients with neuromyelitis optica spectrum disorder and effects of circulating anti-aquaporin-1 antibody level" J. Clin. Neurol., 9: 36-42, (2013).
Kleiter et al., "Neuromyelitis Optica: Evaluation of 871 Attacks and 1,153 Treatment Courses," Ann Neurol, 79(2), 206-216, (Feb. 2016).
Levy et al., "Purified human C1-esterase inhibitor is safe in acute relapses of neuromyelitis optica", Neurology: Neuroimmunology & Neuroinflammation, vol. 1, No. 1, (Jun. 2004).
Levy et al., Neural Neuroimmunol Neuroinflammation 2014;1 :e5, (published Apr. 24, 2014).
Levy, "C1-esterase Inhibitor (Cinryze) for Acute Treatment of Neuromyelitis Optica Exacerbation" Clinical Trial, Received Dec. 29, 2012, Retrieved online from: https://clinicaltrials.gov/ct2/show/study/NCT01759602. Retrieved on Dec. 16, 2015.
Phuan et al., "C1q-targeted monoclonal antibody prevents complement-dependent cytotoxicity and neuropathology in in vitro and mouse models of neuromyelitis optica", Acta Neuropathol., 125: 829-840 (2013).
Pittock et al., "Eculizumab in AQP4-IgG-positive relapsing neuromyelitis optica spectrum disorders: an open-label pilot study", The Lancet, Neurology, 12(6): 554-562, (2013).
Roemer et al., "Pattern-specific loss of aquaporin-4 immunoreactivity distinguishes neuromyelitis optica from multiple sclerosis" Brain, 130, 1194-1205, (2007).
Tradtrantip et al., "Potential Therapeutic Benefit of C1-Esterase Inhibitor in Neuromyelitis Optica Evaluated In Vitro and in an Experimental Rat Model," PLoS One, 9(9), 1-8, (2014).

(Continued)

*Primary Examiner* — Kimberly Ballard
*Assistant Examiner* — Stacey N MacFarlane
(74) *Attorney, Agent, or Firm* — Fangli Chen; Proskauer Rose LLP

(57) ABSTRACT

Compositions and methods useful for the treatment of neuromyelitis optica (NMO) or neuromyelitis optica spectrum disorder (NMOSD) are disclosed.

9 Claims, 1 Drawing Sheet

(56) References Cited

OTHER PUBLICATIONS

URL: https://clinicaltrials.gov/archive/NCT, "C1-esterase inhibitor (Cinryze) for Acute Treatment of Neuromyelitis Optica Exacerbation", Jan. 28, 2013 (retrieved from the internet).
Clinical Trial Identifier NCT01759602, [online] Jan. 2, 2013. Retrieved from: <https://www.clinicaltrials.gov/ct2/show/NCT01759602?term=NCT01759602&rank=1> Retrieved on: May 12, 2018.
Archived History of Changes for NCT01759602 [online] Retrieved from: <https://www.clinicaltrials.gov/ct2/history/NCT01759602> Retrieved on: May 12, 2018.
"C1 Esterase Inhibitor (Human) Dosage," published [on line] Mar. 14, 2010. Retrieved from: <https://www.drugs.com/dosage/c1-esterase-inhibitor-human.html> Retrieved on: Apr. 21, 2017.

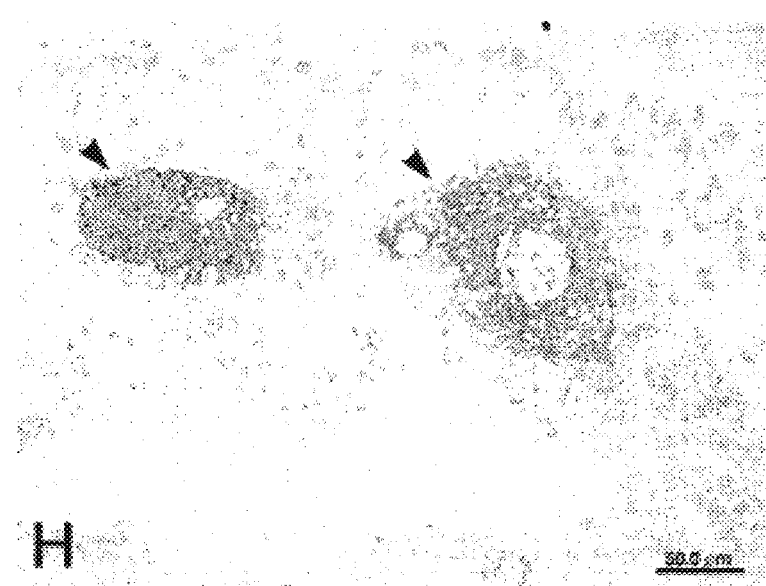

COMPOSITIONS AND METHODS USEFUL FOR THE TREATMENT OF NEUROMYELITIS OPTICA SPECTRUM DISORDERS

CROSS REFERENCE TO RELATED APPLICATIONS

This application is a Continuation Application of U.S. application Ser. No. 16/293,134, filed Mar. 5, 2019, which is a continuation of a U.S. application Ser. No. 14/539,405, filed on Nov. 12, 2014, now patent number U.S. Pat. No. 10,272,142, which claims priority to and the benefit of U.S. Provisional Application No. 61/903,643 filed Nov. 13, 2013, the disclosures of which are hereby incorporated by reference.

FIELD OF THE INVENTION

The invention relates to the fields of central nervous system and neuromyelitis optica (NMO) spectrum disorders. More specifically, the invention provides an anti-inflammatory formulation and methods of use thereof which ameliorate or reduce the symptoms of NMO.

BACKGROUND OF THE INVENTION

Numerous publications and patent documents, including both published applications and issued patents, are cited throughout the specification in order to describe the state of the art to which this invention pertains. Each of these citations is incorporated herein by reference as though set forth in full.

Neuromyelitis optica spectrum disorders (NMOSD) include limited forms of Devic's disease, such as single or recurrent events of longitudinally extensive transverse myelitis, bilateral simultaneous or recurrent optic neuritis, asian optic-spinal multiple sclerosis, optic neuritis associated with systemic autoimmune disease, optic neuritis or transverse myelitis associated with lesions in specific brain areas such as the hypothalamus, periventricular nucleus, and brainstem, and NMO-IgG negative NMO: AQP4 antibody-seronegative NMO.

Neuromyelitis optica (NMO or Devic's disease) is an inflammatory, demyelinating syndrome of the central nervous system that is characterized by severe attacks of optic neuritis and transverse myelitis, which, unlike the attacks in multiple sclerosis, commonly spare the brain in the early stages.

In developed nations, neuromyelitis optica disproportionately strikes non-white populations, in which multiple sclerosis is rare. Neuromyelitis optica presents with clinical, neuroimaging, and laboratory findings that distinguish it from multiple sclerosis. Moreover, the detection of neuromyelitis optica immunoglobulin G (NMO-IgG), an autoantibody, in the serum of patients with neuromyelitis optica, distinguishes neuromyelitis optica from other demyelinating disorders. NMO-IgG binds to aquaporin 4 which is the main channel that regulates water homoeostasis in the central nervous system. NMO-IgG is also detected in the serum of patients with disorders related to neuromyelitis optica, including Asian optic-spinal multiple sclerosis, recurrent transverse myelitis associated with longitudinally extensive spinal cord lesions, recurrent isolated optic neuritis, and optic neuritis or transverse myelitis in the context of certain organ-specific and non-organ-specific autoimmune diseases.

NMO patients are currently treated using agents which reduce symptoms and reduce or prevent relapses. No cure for NMO or NMOSDs is currently available. Most individuals with NMO have an upredictable, relapsing course of disease with attacks occurring months or years apart. Disability is cumulative, the result of each attach damaging new areas of myelin. Clearly, a need exists for improved treatments for this devastating disease which can limit the neurologic dysfunction that results from successive acute relapses of NMO.

SUMMARY OF THE INVENTION

In accordance with the present invention, a method of treating or delaying the progression of a CNS disorder alleviated by inhibiting complement immune system activation in a patient in need of such treatment is disclosed. An exemplary method comprises administering, during an active CNS attack, a therapeutically effective amount of C1-esterase inhibitor (C1-INH) alone or in combination with other agents useful for treatment of such CNS disorders. In a preferred embodiment, the disorder is neuromyelitis optica (NMO) or neuromyelitis optica spectrum disorder (NMOSD). Such treatment can be during the acute phase of onset or soon thereafter and is preferably of short duration.

In one aspect, the C1-esterase inhibitor (C1-INH) comprises a human plasma-derived C1-INH (hC1-INH) or a recombinant C1-INH (rC1-INH) and the disorder is selected from the group consisting of neuromyelitis optica (NMO) or Devic's disease, single or recurrent events of longitudinally extensive transverse myelitis, bilateral simultaneous or recurrent optic neuritis, asian optic-spinal multiple sclerosis, optic neuritis associated with systemic autoimmune disease, optic neuritis or myelitis associated with lesions in specific brain areas such as the hypothalamus, periventricular nucleus, and brainstem, and NMO-IgG negative NMO: AQP4 antibody-seronegative NMO. In a particularly preferred embodiment, the disorder is NMO and said C1 esterase inhibitor is CINRYZE®.

In another aspect of the invention, the C1-INH is administered in combination with another agent useful for treating NMO or NMOSD. Such agents/treatments include without limitation, plasmapheresis and/or administration of intravenous immunoglobulin preparations, administration of mycopohenolate, rituximab and/or eculizubab. In certain approaches, the agents/treatments are administered concurrently. In other approaches, they are administered sequentially.

Also within the scope of the present invention is a pharmaceutical composition for treating or delaying the progression of a disorder caused by alleviated by inhibiting alternative pathway complement immune system activation in a patient in need of such treatment, the composition comprising administration of an activation inhibiting amount of a C1-esterase inhibitor (C1-INH); and optionally, a biologically active agent selected from the group consisting of, intravenous immune therapy, mycopohenolate, rituximab and/or eculizubab or a combination thereof; and a pharmaceutically acceptable carrier medium.

BRIEF DESCRIPTION OF THE DRAWING

FIG. 1 is a photograph (Roemer et al. (2007) Brain 130:1194-1205) showing the classic complement deposition in NMO lesions in both the rim pattern (left) and rosette pattern. Staining is for C9neo.

DETAILED DESCRIPTION OF THE INVENTION

The present invention relates to the discovery that C1-esterase inhibitor (C1-INH) protein may be advantageously administered to NMO and NMOSD patients who present with relapsing autoimmune disease targeting the spinal cord and optic nerve leading to paralysis and blindness. It has been unexpectedly discovered that early short term treatment with C1-INH, as an adjunct to intravenous corticosteroid immunosuppressive therapy (such as IV methylprednisolone) and plasmapheresis in those patients who do not respond to IV steroids ("standard-of-care"), can reduce the damage to the patients nervous system compared to "standard-of-care" alone. As a further advantage to this approach, the present inventors have discovered that early and/or short term duration treatment with C1-INH can produce a durable (longer term) reduction in disease burden post cessation of treatment.

In a preferred embodiment of the invention, the C1-INH is CINRYZE®. A preferred aspect of the invention is where the patients are treated with conventional intravenous immune therapy (e.g., a synthetic glucocorticoid, such as methylprednisolone). In an alternative embodiment, the IV immunotherapy includes other known therapies for treating NMO, for example, plasmapheresis and/or intravenous immunoglobulin preparations. Other approaches include off label uses of anti-lymphocyte preparations, rituximab (antibody against CD20), mycophenolate and/or eculizumab (monoclonal antibody against terminal complement cascade protein C5).

C1 esterase inhibitor (C1-INH) is an endogenous plasma protein (or a functional analog thereof) in the family of serine protease inhibitors (SERPINs) and has broad inhibitor activity in the complement, contact, and coagulation pathways. C1-INH inhibits the classical pathway of the complement system by binding C1r and C1s and inhibits the mannose-binding lectin-associated serine proteases in the lectin pathway. A nanofiltered plasma derived C1-INH (Cinryze®; Viropharma) is FDA approved for routine prophylaxis against angioedema attacks in adolescent and adult patients with hereditary angioedema (HAE), a disease characterized by constitutional deficiency or dysfunction of endogenous C1 esterase inhibitor.

Cinryze® is known to be well tolerated in humans via the experience in patients with HAE studied in randomized trials as well as in an extension trial. The most frequent adverse events reported at the doses used for HAE were headaches and nasopharyngitis. In more than four years of post-marketing surveillance, there have been no safety concerns for infectious events that could be attributed to Cinryze®. Moreover, plasma derived formulations of C1-INH have been evaluated for their clinical use in pilot studies of sepsis, ischemia-reperfusion injury, and capillary leak in bone marrow transplantation. Thus, C1-INH is an ideal therapeutic, either alone or as part of a combination therapy, for diseases that implicate, for example, the classical complement pathway (e.g., antibody-mediated diseases) and of the lectin pathway (e.g., ischemia reperfusion injury).

With respect to the present invention, the C1-INH may be, for example, an isolated human plasma derived C1-INH (hC1-INH) or a recombinant C1-INH (rC1-INH). In a preferred aspect, the C1-INH is rC1-INH.

The following definitions are provided to facilitate an understanding of the present invention.

"Neuromyelitis optica spectrum disorders (NMOSD), include, for example, neuromyelitis optica (NMO) or Devic's disease, limited forms of Devic's disease, such as single or recurrent events of longitudinally extensive transverse myelitis, and bilateral simultaneous or recurrent optic neuritis, asian optic-spinal multiple sclerosis, optic neuritis associated with systemic autoimmune disease, optic neuritis or myelitis associated with lesions in specific brain areas such as the hypothalamus, periventricular nucleus, and brainstem, NMO-IgG negative NMO: AQP4 antibody-seronegative NMO.

As used herein, "administering" refers to a method of delivering a composition of the invention (e.g., Cinryze®) alone and in combination with agents known to be useful for ameliorating NMO and NMOSD symptoms to the patient. Such methods are well known to those skilled in the art and include, but are not limited to, oral, nasal, intravenous, intramuscular, intraperitoneal, subcutaneous, intrathecal, intradermal, or topical administration. The route of administration can depend on a variety of factors, such as the therapeutic goals. Compositions of the invention may be administered on a continuous or an intermittent basis. Methods for formulating and subsequently administering therapeutic compositions are well known to those skilled in the art. See, for example, Remington, 2000, The Science and Practice of Pharmacy, 20th Ed., Gennaro & Gennaro, eds., Lippincott. Williams & Wilkins. The dose administered will depend on many factors, including the mode of administration and the formulation. Typically, the amount in a single dose is an amount that effectively reduces the level of NMO antigenic polypeptides or NMO-specific autoantibodies in an individual without exacerbating the disease symptoms. A preferred feature of the invention entails self administration of C1-INH via systemic (IV) or subcutaneous injection in appropriate dosage forms.

The term "effective amount," as used herein, refers to the quantity of a compound or composition that achieves a beneficial clinical outcome when the compound or composition is administered to a patient. For example, when a composition of the invention is administered to a patient with, intravenous immune therapy (and possibly along with plasmapheresis), a "beneficial clinical outcome" includes the reduction in the neurologic deficits caused by optic neuritis (visual loss/blindness), transverse myelitis (paralysis, sensory loss, loss of bowel/bladder function, potential brainstem dysfunction), and/or other medical sequelae that may result as a consequence of neurologic dysfunction from acute relapses of NMO/NMOSD which could negatively impact the longevity of the patient.

The term "early" as used herein regarding treatment, refers to the timing of treatment which may advantageously occur or be initiated immediately upon attack onset, or within 7 days from the onset of the CNS attack, more preferably within 5 days. A preferred timing is within 72 hours, more preferably within 24 hours, and most preferably within 8 hours of onset of an acute CNS attack. An alternate feature of the invention is where "early" denotes the initiation of treatment of a patient within 24 hours of pro-drome of an acute CNS attack in said patient, more preferably within 8 hours, and more preferably within 4 hours.

As used herein, "short term duration" with regard to treatment, refers to drug treatments which occur between 1 to 10 days, more preferably between 3 to 7 days and most preferably for 5 days.

As used herein, EDSS refers to "The Kurtzke Disability Status Scale (DSS)" which was developed by Dr. John Kurtzke in the 1950s to measure the disability status of people with multiple sclerosis. This scale was modified several times to more accurately reflect the levels of disabilities clinically observed. The scale was renamed the Kurtzke Expanded Disability Status Scale (EDSS). The EDSS provides a total score on a scale that ranges from 0 to 10. The first levels 1.0 to 4.5 refer to people with a high degree of ambulatory ability and the subsequent levels 5.0 to 9.5 refer to the loss of ambulatory ability. The range of main categories include (0)=normal neurologic exam; to (5)=ambulatory without aid or rest for 200 meters; disability severe enough to impair full daily activities; to (10)=death due to MS. In addition, it also provides eight subscale measurements called Functional System (FS) scores. This scale is also is also appropriate for scoring NMO and NMOSD patients.

The term "isolated," as used herein in describing a material, for example, refers to material removed from its original environment (e.g., the natural environment if it is naturally occurring). For example, a naturally-occurring polypeptide (i.e., protein) present in a living animal is not isolated, but the same polypeptide, separated from some or all of the coexisting materials in the natural system, is isolated.

Moreover, the "polypeptides" or "proteins" used in practicing the present invention may be natural proteins, synthesized proteins, or may be preferably recombinant proteins. Further, the proteins described herein can be naturally purified products, or chemically synthesized products, or recombinant products from prokaryotic or eukaryotic hosts (e.g., bacteria, yeast, higher plant, insect, or mammalian cell). Such proteins can be glycosylated or non-glycosylated according to the different hosts used.

Turning to the recombinant proteins used in practicing the invention, the recombinant C1-INH (rC1-INH) proteins can be expressed or produced by conventional recombinant DNA technology, using a polynucleotide sequence specific to C1-INH as known in the art. Generally, such recombinant procedure comprises the following steps:

(1) transfecting or transforming the appropriate host cells with the polynucleotide or its variants encoding C1-INH protein of the invention or the vector containing the polynucleotide;

(2) culturing the host cells in an appropriate medium; and (3) isolating or purifying the protein from the medium or cells.

Regarding the invention more generally, in methods of treating NMO diseases, C1-INH may be used in combination with an additional biologically active agent effective for treating acute relapse of NMO in order to limit the disability from individual attacks and, over time, reduce overall morbidity and disease burden that accrues from multiple attacks of NMO. Moreover, such biologically active agents may not provide complete treatments for NMO disorders and may in fact provide merely a partial or incomplete treatment, such as in the case of eculizumab. Therefore, in certain preferred aspects of the method of the invention, a C1-INH may be administered to a patient in combination with one or more of the agents listed above (e.g., co-administration).

When applying the method of the invention by co-administration, where separate dosage formulations are used, the C1-INH and biologically active agent can be administered concurrently, or separately at staggered times, i.e., sequentially. In practice, the agents of the invention may be administered as separate dosage units or formulated for administration together, according to procedures well known to those skilled in the art. See, for example, Remington: The Science and Practice of Pharmacy, 20th ed., A. Genaro et al., Lippencot, Williams & Wilkins, Baltimore, MD (2000). Preferably, the C1-INH is administered concurrently with the biologically active agent. In other preferred co-administration strategies, the C1-INH may be administered, for example, before administration of the biologically active agent, after administration of the biologically active agent, or concomitantly with the administration of the biologically active agent. Additionally, the C1-INH may be administered concurrently with the biologically active agent where the amount or concentration of the biologically active agent is decreased or tapered with respect to the C1-INH, wherein the amount or concentration of the C1-INH is increased, decreased, or fixed.

Suitable methods of introduction of compositions of the invention to a patient include but are not limited to intradermal, intramuscular, intraperitoneal, intravenous, subcutaneous, intranasal, intraocular, epidural, and oral routes. Moreover, compositions of the invention may be administered by infusion or bolus injection, by absorption through epithelial or mucocutaneous linings (e.g., oral mucosa, rectal, and intestinal mucosa, etc.). Administration may further be systemic or local. And administration can be daily, weekly, monthly, etc.

The orally administered dosage unit may be in the form of tablets, caplets, dragees, pills, semisolids, soft or hard gelatin capsules, aqueous or oily solutions, emulsions, suspensions or syrups. Representative examples of dosage forms for parenteral administration include injectable solutions or suspensions, suppositories, powder formulations, such as microcrystals or aerosol spray. The composition may also be incorporated into a conventional transdermal delivery system.

Additionally, in certain situations, compounds used in practicing the invention may be delivered as pharmaceutical compositions that include a pharmaceutically acceptable carrier medium. For example, the invention includes a pharmaceutical composition for treating or delaying the progression of a NMO disorder alleviated by inhibition of C1 esterase activity, in a patient in need of such treatment, the composition comprising a C1-esterase inhibitor (C1-INH); an additional biologically active agent, such as intravenous immune therapy, mycopohenolate, rituximab and/or eculizubab, or a combination thereof; and a pharmaceutically acceptable carrier medium.

As used herein, the expression "pharmaceutically acceptable carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, 20th edition, A. R. Genaro et al., Part 5, Pharmaceutical Manufacturing. pp. 669-1015 (Lippincott Williams & Wilkins, Baltimore, MD/Philadelphia, PA) (2000)) discloses various carriers used in formulating pharmaceutical compositions and known techniques for the preparation thereof. Except insofar as any conventional pharmaceutical carrier medium is incompatible with the compositions described herein, such as by producing an undesirable biological effect or otherwise interacting in an deleterious manner with any other component(s) of a formulation comprising the active agent(s), its use is contemplated to be within the scope of this invention.

More specifically, in the production of solid dosage forms, the pharmaceutical composition may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. Liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. Suppositories may include excipients, such as vegetable, petroleum, animal or synthetic oils, wax, fat and polyols. Aerosol formulations may include compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further provides controlled-release, sustained-release, or extended-release therapeutic dosage forms for the pharmaceutical composition, in which the composition is incorporated into a delivery system. This dosage form controls release of the active agent(s) in such a manner that an effective concentration of the active agent(s) in the bloodstream can be maintained over an extended period of time, with the concentration in the blood remaining relatively constant, to improve therapeutic results and/or minimize side effects. Additionally, a controlled-release system would provide minimum peak to trough fluctuations in blood plasma levels of the active agent.

Additionally, various delivery systems are known and can be used to administer compositions that comprise C1-INH, or C1-INH in combination with a biologically active agent, such as eculizumab. For example, such compositions may be encapsulated in liposomes, microparticles, and microcapsules, for example.

The methods of the present invention will normally include medical follow-up to determine the therapeutic or prophylactic effect brought about in the patient undergoing treatment with the compound(s) and/or composition(s) described herein.

Turning to the use of C1-INH as a treatment for disease more specifically, C1-INH may be used for treatment of NMO and related neuromyelitis optica spectrum disorders (NMOSD) in vivo. The results of the experiments described in the following example demonstrate that commercially available plasma-derived C1-INH can limit the neurologic disability from individual attacks and, over time, reduce the overall morbidity and disease burden that accrues from multiple attacks of NMO.

The following example is provided to describe the invention in further detail. This example is provided for illustrative purposes only and is not intended to limit the invention in any way.

Example I

CINRYZE® (C1 Esterase Inhibitor [Human]) for the Treatment of Acute Optic Neuritis and/or Transverse Myelitis in Neuromyelitis Optica and Neuromyelitis Optica Spectrum Disorder NMO is a severe, demyelinating autoimmune disease of the central nervous system that preferentially affects the optic nerves and spinal cord. Although historically considered a subtype of multiple sclerosis (MS) with overlapping symptoms, NMO is distinct radiologically and prognostically and has a pathophysiology unresponsive to typical MS treatments (Weinshenker et al., (2007) Arch Neurol 64:899-901); Kimbrough, et al., (2012). In 2004, an antibody targeting the water channel protein, aquaporin-4, was found to be associated with NMO. Compared to MS, NMO exhibits an older age at onset, a poorer prognosis, and a rarity of cerebrospinal fluid oligoclonal IgG bands. NMO attacks typically produce moderate to severe disability that leads to accumulation of disability with each attack; between attacks, patients generally remain neurologically stable without evidence of progressive deterioration. Therefore, it is crucial that aggressive treatment for each relapse is optimized to prevent disability.

NMO affects predominantly females, with a female to male ratio of 6.5:1. The relative frequency of NMO among demyelinating disorders is quite variable, being higher in Asian, Hispanic and African populations and lower among Caucasians. The few population-based prevalence studies of NMO conducted provide prevalence rates of 0.32 to 3.1 per 100,000 in the non-white population (Nandhagopal, et al., (2010) Postgrad Med J 86:153-159).

Clinically definite NMO is defined by a history of optic neuritis and history of transverse myelitis with a non-MS brain MRI, longitudinally extensive myelitis lesions and/or presence of the NMO-IgG biomarker. Seronegative NMO patients with transverse myelitis and optic neuritis must have longitudinally extensive myelitis and a brain MRI that is not typical for multiple sclerosis. Seronegative NMO is a group that has not been adequately characterized for widespread inclusion in clinical trials. A third group, NMOSD, is identified as AQP4 antibody positive individuals with either optic neuritis or transverse myelitis.

NMOSD comprise the spatially limited syndromes of longitudinally extensive transverse myelitis (LETM), recurrent isolated optic neuritis (RION)/bilateral optic neuritis (BON), and Asian opticospinal multiple sclerosis (OSMS), as long as patients test positive for the anti-AQP4 antibody (Sellner, et al., (2010) European J. Neurol 17:1019-1032). Bizzoco, et al., reported that 7 of 13 (56%) NMOSD patients from Tuscany developed clinically definite NMO after a follow-up time of at least 2 years with the other six (46%) remaining NMOSD (Bizzoco et al., (2009) J. Neurol 256: 1891-1898). Weinshenker et al., (supra) prospectively studied 29 patients with a first event of LETM. Within 1 year, 6 of the 11 seropositive (AQP4+) patients had a relapse of myelitis (indicative of recurrent transverse myelitis) or developed optic neuritis (indicative of neuromyelitis optica). By contrast, no seronegative patients relapsed over 1-7 years follow-up. NMO and Asian OSMS have similar neuroimaging, serological, and immunopathological characteristics, and the difference is primarily one of classification as in Japan these individuals are diagnosed with MS, but in North America and Europe, these patients are diagnosed with NMO (Matsuoka, et al., (2007) Brain 130:1206-23; Wingerchuk et al., (2007) Lancet Neurol 6:805-815).

The current standard of care for treatment of acute NMO attacks of both optic neuritis and transverse myelitis is a 5-day course of high dose methylprednisolone (1000 mg daily)(Kimbrough, supra 2012). In some patients, this course of steroid treatment is sufficient to suppress CNS inflammation and reverse some neurologic dysfunction. Factors that may predict success with steroids alone include a small CNS lesion caught early in the process and concurrent preventive immunosuppression. In many patients, steroids are not sufficient to suppress CNS inflammation, and treatment escalation to plasma exchange is necessary. Five cycles of 1.0-1.5 volume exchanges require an additional 2-week inpatient hospitalization and a central line catheter. Plasma exchange carries a 4-10% risk of line infection or thrombotic complications. Despite these risks, plasma exchange is standard of care in steroid-unresponsive patients because it is 50-70% effective in reducing active CNS inflammation and reducing inflammatory damage in this patient population (Szczepiorkowski et al., (2010) J Clin Apher 25(3):83-177). Ultimately, neurologic recovery after high dose steroids and plasma exchange can be stratified into three groups: a group that does not improve at all, a group that improves some but maintains a significant neurologic deficit and a group that improves well if not back to baseline.

The rationale for using C1-esterase inhibitor (CIN-RYZE®) in NMO is based on pathology showing a prominent role for complement in active NMO lesions (Luchinetti et al. (2002) Brain 125:1450-1461; Misu et al. (2007) Brain 130:1224-1234; Roemer et al. (supra, 2007). NMO is not unique in involving complement, which may have a pathogenic role in other demyelinating diseases including multiple sclerosis (Prineas, 2012). However, NMO is characterized by its complement involvement depositing in a rim or rosette pattern in all active lesions (FIG. 1). In vitro, complement is critical in mediating damage initiated by anti-AQP4 antibody binding to astrocytes (Hinson et al., (2007) Neurology 69:2221-2231; Kinoshita et al., (2008) NeuroReport 20(5):508-512). The effector of antibody triggered cell damage is the complement cascade (Marignier et al. (2010) Brain 133:2578-2591; Sabater et al. (2009) J. of Neuroimmunology 215:31-35) and blocking the complement cascade with C1-inhibitor prevents damage ex vivo (Saadoun et al. (2012) Annals of Neurology 71(3):323-333). Based on this mounting evidence the consensus in the field is that prevention of the complement cascade in the CNS would ameliorate the damage caused in NMO inflammatory attacks. This was the basis of the first open label prospective trial in NMO using eculizumab (Soliris®). Results from this trial are now publically available. In contrast to the eculizumab trial, which is a prevention trial, the inventive approach described herein provides for complement inhibition as acute treatment during an active CNS attack. This approach is designed to administer the inhibitory drug when complement damage is at its peak. This approach minimizes the exposure to this medication and dramatically reduces cost of care compared to eculizumab therapy.

Patients with NMO do not lack natural C1-esterase inhibitor, but administering pd C1-INH to increase endogenous levels appears to suppress the complement pathways. Notably, in patients with hyperactive complement activation, this approach has been shown to be beneficial in sepsis and myocardial infarction. In sepsis, complement activation is a contributing factor to end organ failure. Notwithstanding concerns that complement inhibition would prevent bacterial clearance, high dose C1-esterase inhibitor provided to sepsis patients reduced sepsis-induced mortality and all-cause mortality (Ignonin et al., (2012) Crit Care Med 40(3):770-777). In myocardial infarction, complement activation participates in reperfusion injury and induction of inflammation, leading to reduced coronary perfusion. Several studies have shown a benefit of C1 esterase inhibitors in ameriolorating the complement-mediated reperfusion injury (Buerke et al. (1995) Circulation 91:393-402; Shandelya et al. (1993) Circulation 88:2812-2826; Weisman et al. (1990) Science 24:146-151; Fattouch et al. (2007) Eur J Cardiothorac Surg 32(2):326-332) after myocardial infarction. The rationale behind all of these studies is that in patients with otherwise normal complement function, tipping the balance toward complement inhibition can reduce end organ damage in certain disease conditions.

Complement-mediated damage is presumed to account for a significant component of the pathological changes observed in patients with NMO and is supported by ex vivo studies of the role of complement in NMO. Similar to the studies in sepsis and myocardial infarction, the rationale for adding human C1-esterase inhibitor to the treatment for NMO acute exacerbations is to tip the balance toward complement suppression in an effort to reduce complement-mediated neurologic damage.

We conducted an open-label phase 1b safety and proof-of-concept trial in 10 subjects with NMO-IgG seropositive NMO or NMO spectrum disease (NMOSD) who presented with acute transverse myelitis and/or optic neuritis. In addition to treating with 1 gram of daily intravenous methylprednisolone, we infused 2000 Units of C1-esterase inhibitor daily ×3 days beginning on day 1 of hospitalization. The primary outcome measure was safety, and the secondary efficacy measure was change in Expanded Disability Scale Scores (EDSS).

Results

Ten NMO-IgG seropositive subjects were enrolled, 7 of whom presented with acute transverse myelitis and 3 with acute optic neuritis. C1-esterase inhibitor (Cinryze®) proved safe in all 10 NMO subjects with no serious adverse events reported. One subject had a headache during the first infusion. There were no thromboembolic events or related lab abnormalities in any of the subjects. EDSS scores dropped from a median of 4.5 on admission to 4.0 on discharge and then down to 2.5 on 30-day follow up. See Table 1. All but one subject returned to pre-attack EDSS and only one subject required escalation to plasmapheresis.

TABLE I

| Study measurement/timing | EDSS score (median) | EDSS score (mean) |
| --- | --- | --- |
| Baseline (pre-acute NMO attack) | | 2.75 |
| Admission (NMO acute attack) | 4.5 | 5.45 |
| Discharge (post hospitalization) | 4.0 | 4.25 |
| 30-day follow-up | 2.5 | 3.28 |

Paired non-parametric t testing was used to compare pre-treatment EDSS scores to each post treatment EDSS score.

Conclusions

C1-esterase inhibitor (Cinryze®) is a safe add-on therapy for NMO/NMOSD patients presenting with acute transverse myelitis and optic neuritis. The evidence provided herein shows a promising benefit with C1-esterase inhibitor in reducing neurologic disability and improving outcomes.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating or delaying the progression of a central nervous system (CNS) disorder alleviated by inhibiting complement immune system activation in a patient in need of such treatment, the method comprising administering to said patient at the onset of an active CNS attack one or more doses of at least 2000 U of C1-esterase inhibitor (C1-INH) per dose, wherein said disorder is neuromyelitis optica (NMO) or neuromyelitis optica spectrum disorder (NMOSD).

2. The method according to claim 1, wherein the C1-esterase inhibitor (C1-INH) comprises a human plasma-derived C1-INH (hC1-INH) or a recombinant C1-INH (rC1-INH).

3. The method according to claim 1, wherein the disorder is selected from the group consisting of neuromyelitis optica (NMO) or Devic's disease, single or recurrent events of longitudinally extensive transverse myelitis, bilateral simultaneous or recurrent optic neuritis, Asian optic-spinal multiple sclerosis, optic neuritis associated with systemic autoimmune disease, optic neuritis or myelitis associated with lesions in the specific brain areas of the hypothalamus, periventricular nucleus, or brainstem, and NMO-IgG negative NMO:AQP4 antibody-seronegative NMO.

4. The method according to claim 1, wherein said disorder is NMO.

5. A method according to claim 1, wherein said administration is during the early acute phase.

6. A method according to claim 1, wherein said administration is of short term duration.

7. The method according to claim 1, further comprising administering an adjunct treatment additional biologically active agent effective for treating or delaying the progression of a disorder selected from the group consisting of neuromyelitis optica (NMO) or Devic's disease, single or recurrent events of longitudinally extensive transverse myelitis, bilateral simultaneous or recurrent optic neuritis, Asian optic-spinal multiple sclerosis, optic neuritis associated with systemic autoimmune disease, optic neuritis or myelitis associated with lesions in the specific brain areas of the hypothalamus, periventricular nucleus, or brainstem, and NMO-IgG negative NMO:AQP4 antibody-seronegative NMO.

8. The method according to claim 7, wherein said adjunct treatment is selected from intravenous immune therapy, plasmapheresis, administration of mycopohenolate, administration of rituximab, administration of eculizumab, administration of intravenous immunoglobulin preparations, or a combination thereof.

9. The method according to claim 8, wherein the intravenous immune therapy comprises a glucocorticosteroid.

\* \* \* \* \*